United States Patent
Yoo et al.

(10) Patent No.: US 8,556,816 B2
(45) Date of Patent: Oct. 15, 2013

(54) PROVIDING A MEASURING ITEM CANDIDATE GROUP FOR MEASURING SIZE OF A TARGET OBJECT IN AN ULTRASOUND SYSTEM

(75) Inventors: Bong Soo Yoo, Seoul (KR); Jeong I. Kim, Seoul (KR)

(73) Assignee: Samsung Medison Co., Ltd., Kangwon-Do ( * ) Notice: Subject to any disclaimer, the term of this patent is extended or adjusted under 35 U.S.C. 154(b) by 172 days.

(21) Appl. No.: 13/117,479

(22) Filed: May 27, 2011

(65) Prior Publication Data
US 2012/0302885 A1 Nov. 29, 2012

(51) Int. Cl.
*A61B 8/00* (2006.01)
(52) U.S. Cl.
USPC .............. 600/443; 600/437; 600/458; 606/1; 382/103; 382/133; 382/131
(58) Field of Classification Search
USPC ........ 600/437, 443, 458; 606/1; 382/103, 133
See application file for complete search history.

(56) References Cited

U.S. PATENT DOCUMENTS

2004/0106916 A1* 6/2004 Quaid et al. ...................... 606/1
2008/0097209 A1 4/2008 Lee et al.
2010/0215245 A1* 8/2010 Olivan Bescos .............. 382/133
2010/0274132 A1* 10/2010 Kim et al. ...................... 600/443
2012/0170812 A1* 7/2012 Kamiyama ................... 382/103

FOREIGN PATENT DOCUMENTS

| KR | 10-2006-0119260 | 11/2006 |
| KR | 10-2007-0121890 | 12/2007 |
| KR | 10-2008-0035163 | 4/2008 |
| KR | 10-2008-0047042 | 5/2008 |

OTHER PUBLICATIONS

Korean Office Action issued in Korean Patent Application No. 10-2009-0116364 dated Nov. 30, 2011.

* cited by examiner

*Primary Examiner* — Baisakhi Roy
(74) *Attorney, Agent, or Firm* — McDermott Will & Emery LLP

(57) ABSTRACT

Embodiments for providing an elastic image are disclosed. In one embodiment, by way of non-limiting example, an ultrasound system comprises: a user input unit configured to receive user input information from a user; a storage unit configured to store a mapping table associating measuring item information on a plurality of measuring items with a plurality of applications; an ultrasound data acquisition unit configured to acquire ultrasound data corresponding to the target object; and a processing unit configured to form an ultrasound image based on ultrasound data and detect a contour of the target object in the ultrasound image in response to the user input information, the processing unit being further configured to extract at least one of measuring items corresponding to the user input information and the contour from the storage unit to form a measuring item candidate group.

7 Claims, 4 Drawing Sheets

_US 8,556,816 B2_

PROVIDING A MEASURING ITEM CANDIDATE GROUP FOR MEASURING SIZE OF A TARGET OBJECT IN AN ULTRASOUND SYSTEM

TECHNICAL FIELD

The present disclosure generally relates to ultrasound systems, and more particularly to providing a measuring item candidate group for measuring size of a target object in an ultrasound system.

BACKGROUND

Recently, an ultrasound system has been extensively used in the medical field due to its non-invasive and non-destructive nature. Modern high-performance ultrasound imaging systems and techniques are commonly used to produce two dimensional ultrasound images and three-dimensional ultrasound images of internal features of patients.

The ultrasound system may transmit ultrasound signals into a living body and receive ultrasound signals (i.e., ultrasound echo signals) therefrom to form a two-dimensional or three-dimensional ultrasound image.

The ultrasound system may measure the size of a target object (e.g., length, circumference, area, volume, etc.) within the living body to provide measurement information. However, to measure such size, a user may need to perform a series of steps such as selecting one of a plurality of applications, selecting one of a plurality of measuring item groups corresponding to the selected application, selecting one of a plurality of measuring items corresponding to the selected measuring item group, and setting a measuring region for measuring a size of the target object on an ultrasound image.

SUMMARY

Embodiments for forming an elastic image in an ultrasound system are disclosed herein. In one embodiment, by way of non-limiting example, an ultrasound system comprises: a user input unit configured to receive user input information from a user; a storage unit configured to store a mapping table associating measuring item information on a plurality of measuring items with a plurality of applications; an ultrasound data acquisition unit configured to acquire ultrasound data corresponding to a target object; and a processing unit in communication with the user input unit, the storage unit and the ultrasound acquisition unit, the processing unit being configured to form an ultrasound image based on ultrasound data and detect a contour of the target object in the ultrasound image in response to the user input information, the processing unit being further configured to extract at least one of measuring items corresponding to the user input information and the contour from the storage unit to form a measuring item candidate group.

In another embodiment, there is provided a method of providing a measuring item candidate group for measuring a size of a target object, comprising: a) acquiring ultrasound data corresponding to the target object; b) forming an ultrasound image based on the ultrasound data; c) receiving user input information from a user; d) detecting a contour of the target object in the ultrasound image in response to the input information; and e) extracting at least one of measuring items corresponding to the user input information and the contour from a mapping table associating information on a plurality of measuring items with a plurality of applications.

In yet another embodiment, there is provided a computer readable medium comprising computer executable instructions configured to perform the following acts: a) acquiring ultrasound data corresponding to a target object; b) forming an ultrasound image based on the ultrasound data; c) receiving user input information from a user; d) detecting a contour of the target object in the ultrasound image in response to the input information; and e) extracting at least one of measuring items corresponding to the user input information and the contour from a mapping table associating measuring item information on a plurality of measuring items with a plurality of applications.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
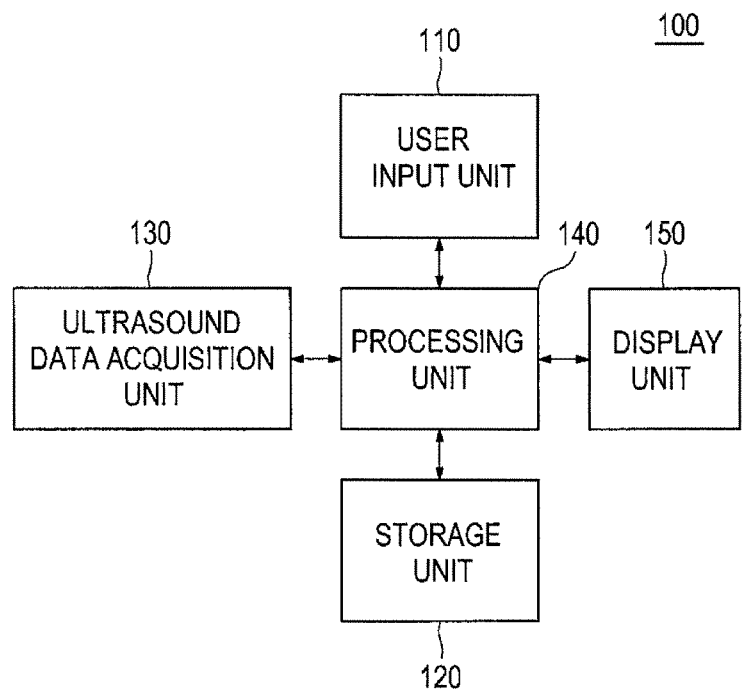
FIG. 1 is a block diagram showing an illustrative embodiment of an ultrasound system.

Referring to FIG. 1, an ultrasound system 100 in accordance with an illustrative embodiment is shown. As depicted therein, the ultrasound system 100 may include a user input unit 110. The user input unit 110 may be configured to receive input information from a user. In one embodiment, the input information may include first input information for setting a caliper for measuring the size (e.g., length, circumference, area, volume, etc.) of a target object within a living body on an ultrasound image, as well as second input information for selecting one of a plurality of diagnostic parts (i.e., numerous applications) of the target object. The input information may further include third input information for selecting one of the measuring items from a measuring item candidate group. The measuring item and the measuring item candidate group are described below in detail. The user input unit 110 may include a control panel, a mouse, a trackball, a keyboard and the like.

The ultrasound system 100 may further include a storage unit 120. The storage unit 120 may store a mapping table associating information ("measuring item information") on a plurality of measuring items with a plurality of applications. In one embodiment, the measuring item information may include a plurality of measuring item groups corresponding to the respective applications, a plurality of measuring items corresponding to the respective measuring item groups and measuring sample values corresponding to the respective measuring items, as shown in Table 1.

TABLE 1

| | Measuring item information | | |
|---|---|---|---|
| Application | Measuring item | Measuring item | Measuring |
| Obstetrics | Fetal biometry measurement | Gestational sac dimension | 10 |
| | | Crown-rump length | 15 |
| | | Biparental diameter | 11 |
| | | ... | ... |
| | Fetal cranium measurement | Outer ocular diameter | 21 |
| | | Inter ocular diameter | 16 |
| | | Nuchal translucency | 19 |
| | | ... | ... |
| | ... | ... | ... |
| Cardiac | Two-dimensional mode | Aortal/left atrium | 40 |
| | | Left ventricle mass | 28 |
| | | Simpson | 99 |
| | | ... | ... |
| | Color Doppler mode | Aortic valve regurgitation | 39 |
| | | Mitral valve regurgitation | 65 |
| | | ... | ... |
| | ... | ... | ... |
| ... | ... | ... | ... |

Also, the measuring item information may further include contour samples corresponding to the respective measurement items. The contour sample may include a two-dimensional contour sample or a three-dimensional contour sample.

The storage unit 120 may also store information (e.g., age, birth date, sexuality, diagnostic day and time, diagnostic application, measuring value, etc.) on the target object.

The ultrasound system 100 may further include an ultrasound data acquisition unit 130. The ultrasound data acquisition unit 130 may be configured to transmit ultrasound signals into the living body and receive ultrasound signals (i.e., ultrasound echo signals) from the living body to thereby output ultrasound data.

Figure 2:
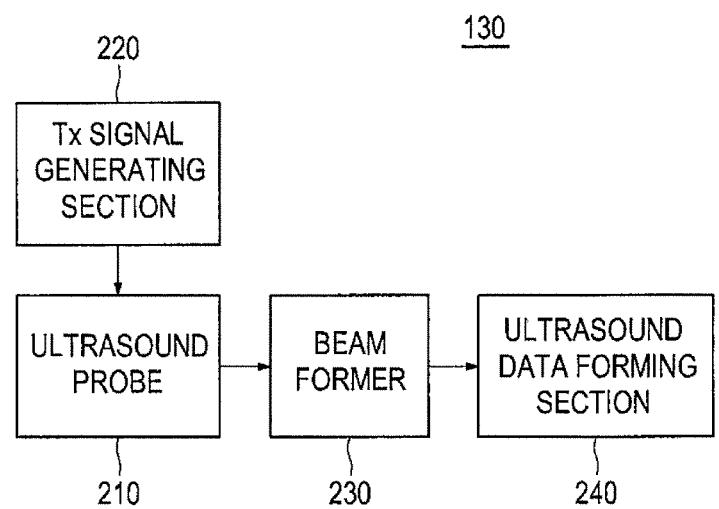
FIG. 2 is a block diagram showing an illustrative embodiment of an ultrasound data acquisition unit.

FIG. 2 is a block diagram showing an illustrative embodiment of the ultrasound data acquisition unit 130. Referring to FIG. 2, the ultrasound data acquisition unit 130 may include an ultrasound probe 210, a transmit (Tx) signal generating section 220, a beam former 230 and an ultrasound data forming section 240.

The ultrasound probe 210 may include a plurality of elements (not shown) for reciprocally converting between ultrasound signals and electrical signals. The ultrasound probe 210 may be configured to transmit ultrasound signals to the living body. The ultrasound probe 210 may be further configured to receive ultrasound echo signals from the living body to thereby output electrical signals ("received signals"). The received signals may be analog signals. The ultrasound probe 210 may include a three-dimensional mechanical probe or a two-dimensional array probe. However, it should be noted herein that the ultrasound probe 210 may not be limited thereto.

The Tx signal generating section 220 may be configured to control the transmission of the ultrasound signals. The Tx signal generating section 220 may be further configured to generate electrical signals ("Tx signals") in consideration of the elements and focal points. Thus, the ultrasound probe 210 may convert the Tx signals provided from the Tx signal generating section 220 into the ultrasound signals, transmit the ultrasound signals to the living body and receive the ultrasound signals from the living body to thereby output the received signals.

Figure 3:
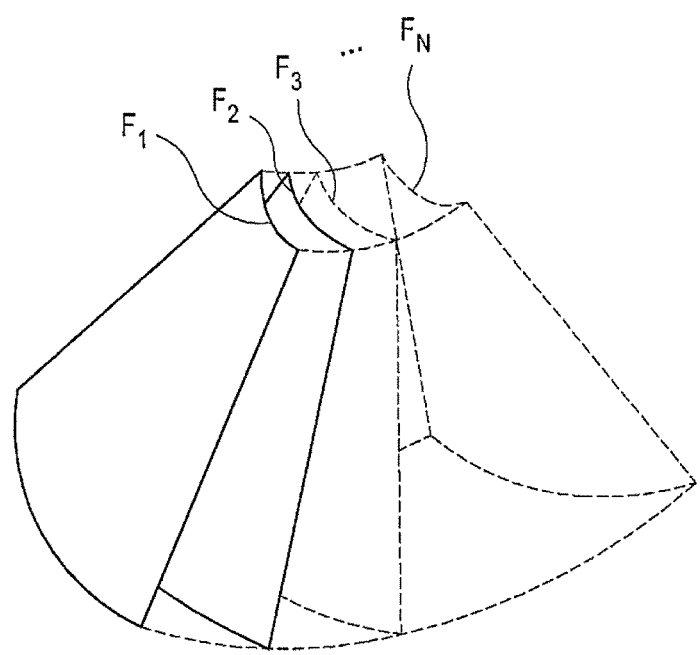
FIG. 3 is a schematic diagram showing an example of acquiring ultrasound data corresponding to a plurality of frames.

In one embodiment, the Tx signal generating section 220 may be configured to Tx signals for obtaining a plurality of frames $F_i$ ($1 \leq i \leq N$) corresponding to a three-dimensional ultrasound image at every predetermined time, as shown in FIG. 3. The frame may include a brightness mode image. However, it should be noted herein that the frame may not be limited thereto.

FIG. 3 is a schematic diagram showing an example of acquiring ultrasound data corresponding to the plurality of frames $F_i$ ($1 \leq i \leq N$). The plurality of frames $F_i$ ($1 \leq i \leq N$) may represent sectional planes of the living body (not shown).

Referring back to FIG. 2, the beam former 230 may be configured to convert the received signals provided from the ultrasound probe 210 into digital signals. The beam former 230 may be further configured to apply delays to the digital signals in consideration of the elements and focal points to output digital receive-focused signals.

The ultrasound data forming section 240 may be configured to form ultrasound data corresponding to the frames $F_i$ ($1 \leq i \leq N$) based on the digital receive-focused signals provided from the beam former 230. The ultrasound data forming section 240 may further perform various signal processing (e.g., gain adjustment) upon the digital receive-focused signals.

Referring back to FIG. 1, the ultrasound system 100 may also include a processing unit 140 in communication with the user input unit 110, the storage unit 120 and the ultrasound data acquisition unit 140. The processing unit 140 may include a central processing unit, a microprocessor or a graphic processing unit. However, it should be noted herein that the processing unit 140 may not be limited thereto.

Figure 4:
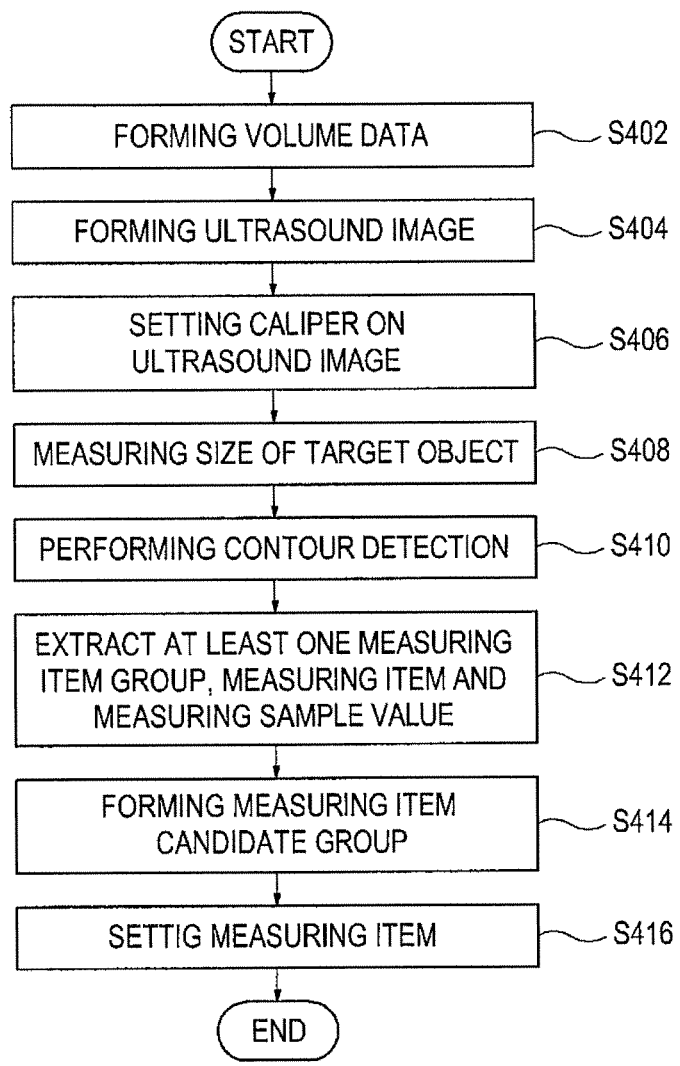
FIG. 4 is a flow chart a process of providing a measuring item candidate group for measuring a size of a target object.

FIG. 4 is a flow chart showing a process of providing a measuring item candidate group for measuring the size of a target object. The processing unit 140 may be configured to synthesize the ultrasound data corresponding to the plurality of frames $F_i$ ($1 \leq i \leq N$) to form volume data VD as shown in FIG. 5, at step S402 in FIG. 4.

Figure 5:
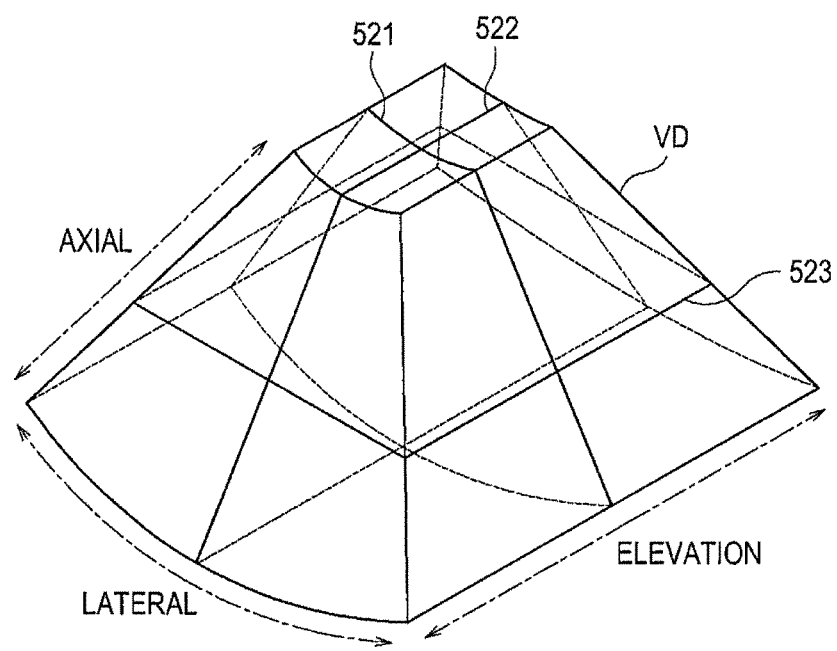
FIG. 5 is a schematic diagram showing an example of volume data.

FIG. 5 is a schematic diagram showing an example of the volume data VD. The volume data VD may include a plurality of voxels (not shown) having brightness values. In FIG. 5, reference numerals 521, 522 and 523 represent an A plane, a B plane and a C plane, respectively. The A plane 521, B plane 522 and C plane 523 may be mutually orthogonal. Also, in FIG. 5, the axial direction may be a Tx direction of the ultrasound signals, the lateral direction may be a longitudinal direction of the elements, and the elevation direction may be a swing direction of the elements, i.e., a depth direction of the three-dimensional ultrasound image.

The processing unit 140 may be configured to form an ultrasound image based on the volume data VD, at step S404 in FIG. 4. In one embodiment, the ultrasound image may include the three-dimensional ultrasound image or the two-dimensional ultrasound image corresponding to each of the A plane 521 to the C plane 523. However, it should be noted herein that the ultrasound image may not be limited thereto. The ultrasound image may be displaced on a display unit 150. Thus, the user may set the caliper on the ultrasound image displayed on the display unit 150 by using the user input unit 110.

The processing unit 140 may be configured to set the caliper on the ultrasound image based on the input information (i.e., second input information) provided from the user input unit 110, at step S406 in FIG. 4.

The processing unit 140 may be configured to measure the size of the target object based on the caliper to form measurement information, at step S408 in FIG. 4. The measurement information may be stored in the storage unit 120.

The processing unit 140 may be configured to perform a contour detection upon the ultrasound image to detect a contour of the target object, at step S410 in FIG. 4. The contour may be detected by using a contour detecting mask such as a Sobel mask, Prewitt mask, Robert mask, Canny mask and the like. Also, the contour may be detected by using a structure tensor.

The processing unit 140 may be configured to retrieve the storage unit 120 to extract at least one measuring item corresponding to at least one of the input information (i.e., first input information), measurement information and contour, at step S412 in FIG. 4.

The processing unit 140 may be configured to arrange the extracted measuring item in an order of similarity with the input information, measurement information and contour to form a measuring item candidate group, at step S414 in FIG. 4. The measuring item candidate group may be displayed on the display unit 150. Thus, the user may select a measuring item from the measuring item candidate group displayed on the display unit 150 by using the user input unit 110.

The processing unit 140 may be configured to select a measuring item corresponding to the input information (i.e., third input information) to set the measuring item, at step S416 in FIG. 4. The selected measuring item may be stored in the storage unit 120.

Referring back to FIG. 1, the ultrasound system 100 may further include the display unit 150. The display unit 150 may display the ultrasound image formed by the processing unit 140. The display unit 150 may also display the measuring item candidate group.

In another embodiment, the present invention may provide a computer readable medium comprising computer executable instructions configured to perform the following acts: a) acquiring ultrasound data corresponding to a target object; b) forming an ultrasound image based on the ultrasound data; c) receiving user input information from a user; d) detecting a contour of the target object in the ultrasound image in response to the input information; and e) extracting at least one of measuring items corresponding to the user input information and the contour from a mapping table associating measuring item information on a plurality of measuring items with a plurality of applications. The computer readable medium may comprise a floppy disk, hard disk, memory, compact disk, digital video disk, etc.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
 a user input device configured to receive user input information for setting a caliper and selecting one of the plurality of applications from a user;
 a storage device configured to store a mapping table associating measuring item information including a plurality of measuring items, a plurality of measuring sample values corresponding to the measuring items and a plurality contour samples corresponding to the measuring items with a plurality of applications;
 an ultrasound data acquisition device configured to acquire ultrasound data corresponding to a target object; and
 a processor in communication with the user input device, the storage device and the ultrasound data acquisition device, the processor being configured to form an ultrasound image based on ultrasound data, set a caliper on the ultrasound image based on the user input information, measure the size of the target object based on the caliper to form measurement information, perform a contour detection upon the ultrasound image to detect a contour of the target object in the ultrasound image in response to the user input information, the processor being further configured to retrieve the storage device to extract at least one of measuring items corresponding to the user input information, the measurement information and the contour from the storage device, and arrange the extracted measuring item in an order of similarity with the input information, the measurement information and the contour to form a measuring item candidate group.

2. The ultrasound system of claim 1, wherein the processing device is configured to:
 form volume data based on the ultrasound data;
 form the ultrasound image based on the volume data.

3. The ultrasound system of claim 1, wherein the user input device is further configured to receive third input information for selecting one of the measuring items from the measuring item candidate group.

4. The ultrasound system of claim 3, wherein the processor is further configured to select the measuring item corresponding to the third input information to set the measuring item.

5. A method of providing a measuring item candidate group, comprising:
 a) acquiring ultrasound data corresponding to a target object;
 b) forming an ultrasound image based on the ultrasound data;
 c) receiving user input information for setting a caliper and selecting one of the plurality of applications from a user;
 d) setting a caliper on a ultrasound image based on the user input information;
 e) measuring the size of the target object based on the caliper to form measurement information;
 f) performing a contour detection upon the ultrasound image to detect a contour of the target object in the ultrasound image in response to the input information;
 g) retrieving a storage device for storing a mapping table associating measuring item information including a plurality of measuring items, a plurality of measuring sample values corresponding to the measuring items and a plurality contour samples corresponding to the measuring items with a plurality of applications, to extract at least one of measuring items corresponding to the user input information, the measurement information and the contour from the storage device; and
 h) arranging the extracted measuring item in an order of similarity with the input information, the measurement information and the contour to form a measuring item candidate group.

6. The method of claim 5, further comprising:
 receiving selection information for selecting one of the measuring items from the measuring item candidate group from the user; and
 selecting the measuring item corresponding to the selection information to set the measuring item.

7. A non-transitory computer readable medium comprising computer executable instructions configured to perform following acts:
 a) acquiring ultrasound data corresponding to a target object;

b) forming an ultrasound image based on the ultrasound data;

c) receiving user input information for setting a caliper and selecting one of the plurality of applications from a user;

d) setting a caliper on the ultrasound image based on the user input information;

e) measuring the size of the target object based on the caliper to form measurement information;

f) performing a contour detection upon the ultrasound image to detect a contour of the target object in the ultrasound image in response to the input information;

g) retrieving a storage device for storing a mapping table associating measuring item information including a plurality of measuring items, a plurality of measuring sample values corresponding to the measuring items and a plurality contour samples corresponding to the measuring items with a plurality of applications, to extract at least one of measuring items corresponding to the user input information, the measurement information and the contour from the storage device; and h) arranging the extracted measuring item in an order of similarity with the input information, the measurement information and the contour to form a measuring item candidate group.

* * * * *